United States Patent [19]

Turner et al.

[11] 4,275,600
[45] Jun. 30, 1981

[54] TESTING RUBBER

[75] Inventors: Donald M. Turner, Bath; Richard Smith, Melksham, both of England

[73] Assignee: Avon Rubber Company Limited, Melksham, England

[21] Appl. No.: 35,511

[22] Filed: May 3, 1979

[30] Foreign Application Priority Data

May 9, 1978 [GB] United Kingdom ............... 18546/78

[51] Int. Cl.³ .............................................. G01N 3/24
[52] U.S. Cl. ...................................... 73/843; 73/15.6
[58] Field of Search ................... 73/843, 847, 15.6, 59

[56] References Cited

U.S. PATENT DOCUMENTS 3,435,666  4/1969  Fann ..................................... 73/59 X

FOREIGN PATENT DOCUMENTS 1196868   7/1970  United Kingdom .
1251560  10/1971  United Kingdom .
1272522   5/1972  United Kingdom .
1286089   8/1972  United Kingdom .

Primary Examiner—Jerry W. Myracle
Attorney, Agent, or Firm—Kenyon and Kenyon

[57] ABSTRACT

Apparatus and method for testing unvulcanized rubber or rubber-like materials can work at high shear rates (e.g. 100 sec$^{-1}$) as a result of applying and maintaining pressure on the test sample as it is being sheared by a rotor in a test chamber. The rotor is smooth-faced. Both conditions simulate more accurately the forces acting on such materials in such operations as extrusion.

The test material is transferred into the test chamber through transfer ports from a transfer chamber by a pressure member which continues to exert pressure on material in the transfer chamber, which may be a next test sample.

Specific operating steps of the rotor at varying speeds and directions to assess various useful parameters of the test material (including not only viscosity but also elasticity) are described, together with a mathematical model for rationalizing the behavior of the material under these test conditions.

13 Claims, 5 Drawing Figures

TESTING RUBBER

FIELD OF THE INVENTION

This invention relates to the testing of unvulcanized rubber and within the term "rubber" we include natural and synthetic rubbers and other elastomers having the properties of unvulcanized rubber.

BACKGROUND OF THE INVENTION

The purpose of the testing of unvulcanized rubber is for the better assessment and control of its behaviour during manufacturing processes such as calendering and extrusion.

The machine used at present for such testing is the Mooney Rheometer. It is a standard machine in the industry in spite of the fact that it has been recognized for some considerable time that it has deficiencies most notably that it works at a low shear rate, approximately 1 reciprocal second, whereas during extrusion of the rubber is subjected to a shear in the region of 100 sec$^{-1}$ and during injection moulding 1000 sec$^{-1}$. It is inherent in the Mooney machine that it cannot be efficiently operated at high shear rates.

The sample to be tested is placed in the rotor chamber and a closure is applied to the chamber. Usually excess material is placed in so that when the two halves of the chamber are closed together the excess has to escape between the lands of the two halves. Not only does this eventually cause wear and loss in precision in the chamber as well as uncertainty as to the precise size of the chamber but this also means that no ascertainable pressure is exerted or maintained on materials in the chamber.

A machine working on the principle of the Mooney can only be used to measure viscosity. In some processes, especially extrusion, the elasticity of the rubber has a pronounced effect on the product and this shows that a test instrument is needed which operates at higher shear rates and which will also convey information on the elastic properties of the rubber being tested. Within the invention this is done not only by providing a test machine but also a test method operable by means of that machine which reveals knowledge about other characteristics of the rubber.

SUMMARY OF THE INVENTION

In order to be able to work at high shear rates we therefore provide a machine and a test method in which the test sample to which a test rotor is to be applied is confined in a test chamber under a controlled and maintained pressure. Then, pressure can be exerted on the sample which is being worked on by the rotor in the chamber such that fracturing within the rubber or slip between the rubber and rotor occurs in a controlled and reproducible way.

In the invention, loading of the material into the test chamber is most effectively carried out by a transfer mechanism whereby ascertained pressure may cause transfer of material from a transfer chamber into the test chamber while the latter is closed and therefore of ascertained volume, and continued pressure on material (either the same as the material under test or the next sample to be tested) in the transfer chamber will continue to be exerted through the transfer ports on the material in the test chamber.

After testing, the test chamber will be opened and the test sample removed. The chamber is then closed again and thereafter the next test material will be transferred through transfer ports of the chamber. The presence in this next test material of small sprues from the transfer ports which are of the first test material will not cause any serious deviations in results obtained for the next test material.

It is a further advantage of the transfer introduction of material into the chamber that the rubber surfaces which come into contact with the rotor will be fresh surfaces and uncontaminated. This is because it will be fresh and uncontaminated rubber surfaces that will also come into contact with the wall parts of dies or other elements in production machines, and so conditions in those machines will be simulated.

Using a machine embodying the invention we have found it possible to give consistent results at shear rates up to 100 sec$^{-1}$. Working at rates higher than this was inhibited only by problems of temperature control within the chamber and there did not seem to be underlying reason why testing under pressure should not, with efficient temperature control, be applied at higher shear rates within machines and methods embodying the present invention.

To use the present machine to give not only viscosity but also other useful information and particularly elasticity information, the machine is first run at a comparatively high shear rate for a given time. During the latter period of this time information upon the viscosity of the rubber is obtained. Then, the drive on the rotor is released and the rubber is allowed to "recover" and rotate the rotor in the reverse direction. This gives direct information on the elastic strains present in the rubber. Then the rotor is rotated at two different speeds both giving a comparatively low shear rate as compared to the first mentioned shear rate but the two shear rates differing by a substantial factor, for example a factor of 5. Comparison of the torque on the rotor at these two lower speeds compared with the two speeds gives a measure of the degree to which the flow behaviour of the rubber deviates from classical or Newtonian behaviour.

DESCRIPTION OF THE DRAWINGS

A particular embodiment of the invention and method of carrying out test methods will now be described with reference to the accompanying drawings wherein.

DESCRIPTION OF A PREFERRED EMBODIMENT

Figure 1:
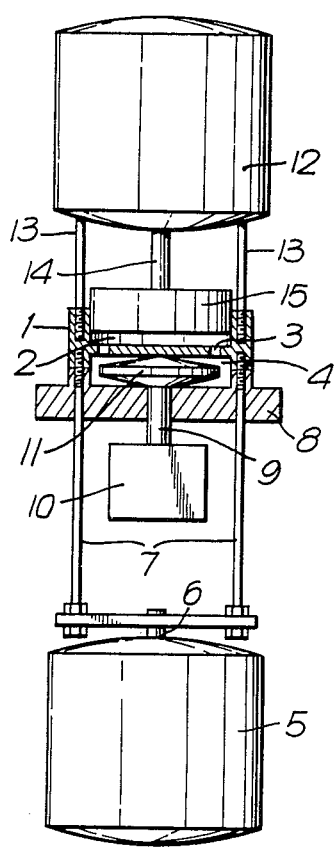
FIG. 1 is a diagrammatic side view of the test apparatus.
Figure 2:
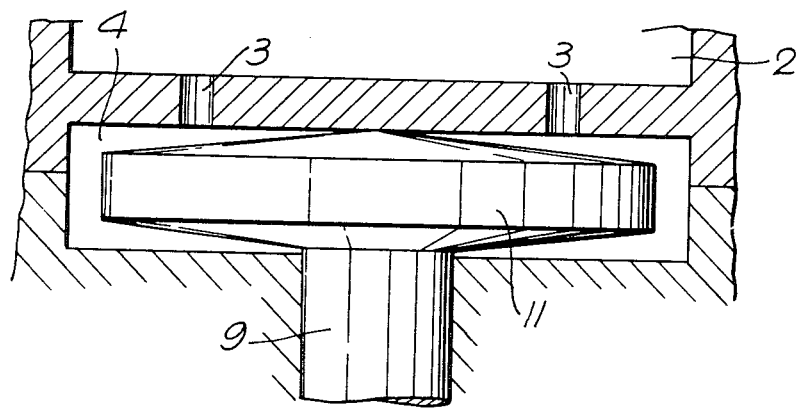
FIG. 2 is a side view of a rotor.
Figure 3:
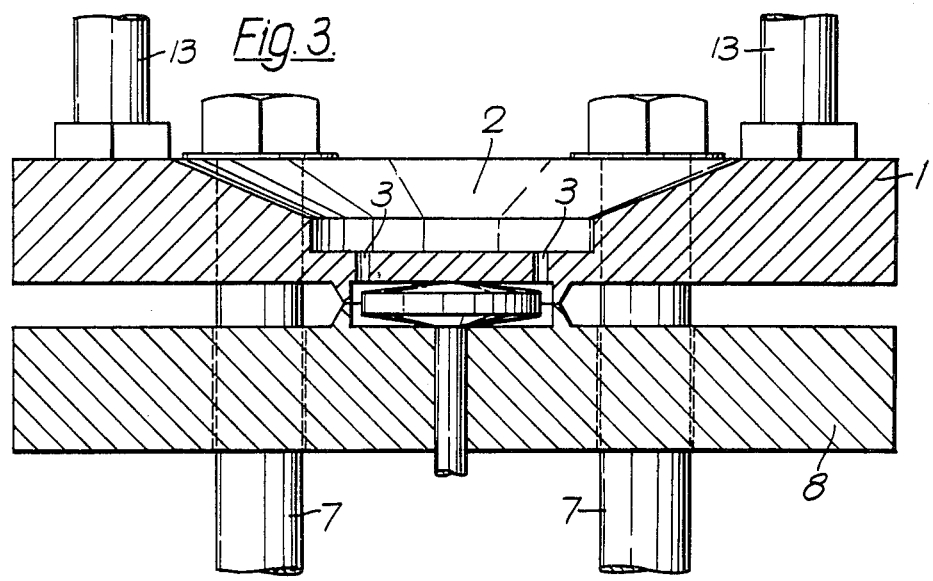
FIG. 3 is a side view in more detail showing the transfer arrangement into the chamber.

Referring first to FIGS. 1, 2 and 3 an element 1 which provides a transfer chamber 2, transfer ports 3 and the upper part of a test chamber 4 is secured by rods 7 to a piston rod 6 of a piston and cylinder 5. The rods 7 penetrate bores in a member 8 which has a plane annular face mating with a similar face on the element 1 and which when its face is so mated defines the lower half of the test chamber 4. The member 8 is tied, by means not shown, to the cylinder of the piston and cylinder 5. A rotor stem 9 penetrates the member 8 and a drive, recovery and torque measuring mechanism 10 for the rotor stem is secured to it. A rotor 11 is mounted on the head of the rotor stem 9 to occupy much of the test chamber 4 when closed. Extension of the piston 6 out of its cylinder will open the test chamber 4 by raising the member 1 from the member 8, and closing of the chamber can be accomplished by withdrawal of the piston 6.

A pneumatic cylinder 12 of a second cylinder and piston arrangement is tied by rods 13 to the member 1 and has on its piston rod a transfer ram 15 which can enter into the transfer chamber 2.

The transfer ports 3 lead from the transfer chamber into the test chamber.

The conformation of the rotor, as seen in FIG. 3 is biconical. This shape is known per sè for the rotor of a shear assessment machine but conventionally such rotors have a roughened surface for example with ridges whereas within the present invention such a rotor may, in suitable circumstances and due to the exertion of pressure during working, be made with smooth surfaces. A comparison between behaviors when rough and smooth rotors are used allows estimation of the wall-slip occurring at the smooth surface.

To charge the test chamber, this being assumed to be empty, a sample of unvulcanized rubber test material is placed in the transfer chamber 2. This will be held at the temperature of the test chamber. When the sample has come to the desired temperature of the test (characteristically around 100° C.) piston rod 14 is urged downwardly and the ram 15 causes transfer of the material through the transfer port 3 into the test chamber 4. The quantity of the sample placed in the transfer chamber 2 will always be greater than the unoccupied volume of the test chamber 4 and hence a residue of the material will be left in the transfer chamber and will continue to be acted on by the transfer ram 15. Thus the pressure exerted on that material by the ram will be communicated through the material in the transfer ports to the material in the test chamber. Normally, the transfer ram will be temporarily withdrawn before the test run is made, excess material of that sample be removed from the transfer chamber, (sprues of that test material being left in the transfer ports) and the next test sample be placed in the transfer pot, with pressure then being reexerted through the transfer ram. This means that the next test sample is being brought to test temperature during the testing of the previous sample and is used to exert pressure on that previous sample.

The rotor is rotated and test manoeuvres are executed as will be described later. At the end of the test on that material, the test chamber is opened by moving the member 1 upwardly away from the lower member 8 and the sample removed manually from the open chamber. It is then closed again and after it has been closed the next sample is introduced by operation of the transfer ram. It can be seen that since the introduction is not carried out until after the chamber has been closed the chamber is of known volume and dimensions and there is no risk of the extrusion of a thin layer of material between the annular land surfaces of members 1 and 8.

The configuration shown in FIG. 1 illustrates the machine being operated by two pressure cylinders. It is possible to obtain the desired operation with a single cylinder, in which case the diameter of the transfer chamber must exceed the diameter of the rotor chamber. The appropriate opening and closing sequence may be obtained by a series of die rods and springs.

Figure 4:
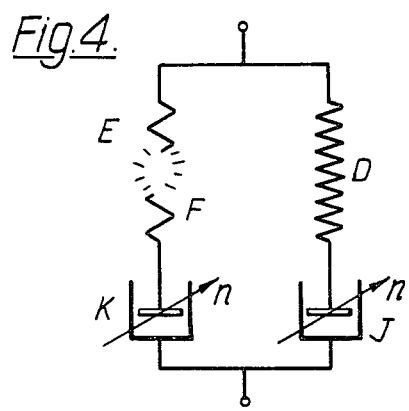
FIG. 4 shows a mathematical model used in assessing rubber behaviour and FIG. 5 is a graph illustrating behaviour of rubber in the apparatus.

FIG. 4 shows a mathematical model which will be used, as we shall now explain, to enable the assessment of rubber characteristics from test procedures in the apparatus just described.

Such a model is not to be taken as literal representation of rubber but more as a guide to the arrangement of the terms in the constitutive equations. The model comprises two Maxwell elements in parallel. E, (associated with time-dependent recovery) and D (associated with immediate recovery), are the elastic moduli of two linear springs and D is normally between 5 and 20 times the magnitude of E. The viscous elements are characterised by constants J and K which give stresses in accordance with the equations $$\sigma_J = J\dot{\gamma}^n$$

$$\sigma_K = K\dot{\gamma}^n$$

where $\dot{\gamma}$ is the shear rate or the extension rate. When the material is subjected to a high stress the fracture limit F of the E spring will be exceeded and then the external stresses on the model will be reset at zero. These six parameters E,D,J,K,F and n can be used to predict the behaviour of unvulcanized rubber in a range of common test and processing situations, and if they are known then it is possible to predict fully the behaviour of unvulcanized rubber in most processing situations. The test apparatus enables the six parameters to be deduced in the most convenient and efficient way.

To obtain the required data it is necessary to make the rotor perform a series of operations. According to the quality of information required, so the number of operations can be changed but the following is an example:

1. Run at 40 r.p.m. for 1 minute to eliminate thixotropic effects in the sample and record final stress $S_{40}$.

2. Immediately on completion of the 40 revolutions the drive on the rotor is disconnected and the rotation of the rotor in the reverse direction is measured. The total recovered shear strain at 20 secs. $R_{20}$ is recorded.

3. The machine is restarted at 0.5 r.p.m. and the stress is continuously recorded relative to the rotation of the rotor until a final steady state stress $S_{0.5}$ is reached.

4. The machine is now run at 0.1 r.p.m. and the stress $S_{0.1}$ is noted when a steady value has been reached.

The above values are not critical and have been selected to illustrate the procedure. 3 and 4 may be interchanged, if required, according to the characteristics of the material.

The results of this sequence are used in the following way:

a. The non-Newtonian index n is calculated from the formula:

$$n = (\log S_{0.5} - \log S_{0.1})/\log 5$$

Figure 5:
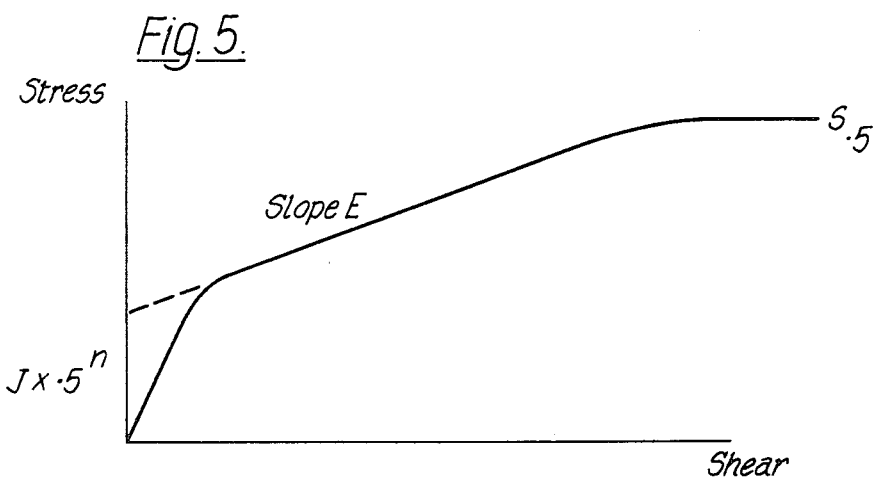

(5 is the ratio in this case between the 3rd and 4th rates)

b. The result in test sequence 3 is illustrated in FIG. 5. If the straight part of the experimental line is extrapolated back to zero, the intercept on the Y axis is the value $J \times 0.5^n$, hence J. The slope of the line is E. The initial slope is $1/(D+E)$, hence D. The final stress $S_{0.5} = (J+K)0.5^n$, hence K.

c. The fracture stress is calculated from the equation $$F = 2(S_{40} - J40^n)$$

These calculations are a simplification and do depend on the material behaving in an ideal way. However, the numbers generated in this way constitute a consistent statement about a sample of material and will reveal any differences in behaviour.

When relating test results to the practical situations in the factory to minimise systematic errors, it is always desirable that the test should correspond as closely as possible to the conditions in the process. Control of the temperature generated by rubber during extrusion is vital and, therefore, the quantity $S_{40}$ will be extremely valuable as a control number for extrusion.

It should be noted that a measurement was made of the recovered shear but this has not been used to calculate the basic parameters. Recovered shear does bear a close relation with extrusion shrinkage, but it does not identify totally with it. A control index for extrusion shrinkage L can be deduced from the above procedure by using the formula $$L = R_{20}/(1 = F/CE)$$

C is a constant depending upon extrusion condition. For a typical tread line it would be between 1.5 and 2.

The calculation of these numbers can be done very rapidly by a programmable calculator. The best arrangement is to connect the test instrument on line to a mini computer. Rather than drawing the graph for sequence b the stress can be recorded at four selected shears and the parameters calculated directly from the equations.

In order to clarify the procedure, the use of such an instrument for controlling the results of tread stocks for extrusion can be considered;

1. The instrument combined with the calculator provides the $S_{40}$ number which is a guide to the temperature generated during extrusion and an extrusion shrinkage number L which is a guide to the shape of the extrudate. The material will be passed or failed according to whether these two numbers are within limits.

2. The instrument will also generate the six parameters and these will give a good guide to the reasons why a sample failed. Information can then be fed back so that corrections can be made to avoid similar defective batches being produced.

3. The information which has been generated gives a very good guide as to how the defective material should be disposed of. Borderline material may be used without problems if selectively blended.

For process control a stream-line procedure is adopted, but as stated earlier if data is required for the design of a process or if a full investigation is required into the suitability of a new material then extra tests and extra analyses may be done.

Some rubber materials show particularly complex thixotropic effects. In these situations it is necessary that tests are done where the material has had a similar history to that in the process. The instrument which has been proposed for the process control tests is capable of providing suitable histories which correspond to those in the process. Extra tests may, therefore, be done at different shear rates. Strain recovery, in particular, is capable of yielding further information. If strain recovery is examined in the region where the stress moves through the fracture region then information is given on the degree of homogeneity in the fracture stress distribution.

We claim:

1. In apparatus for testing a material selected from the group consisting of unvulcanized natural rubber, unvulcanized synthetic rubber and elastomers having the same properties as unvulcanized rubber, said apparatus having a test chamber and a rotor in the test chamber, the improvement comprising wall means defining an ascertained fixed volume for the test chamber, at least one transfer port through a wall of the test chamber for rendering the transfer chamber in communication with the test chamber, means for exerting pressure on material in the transfer chamber, whereby a controlled pressure can be applied to and maintained on material in the test chamber through the at least one transfer port, and sensor means for recording back-rotation of the rotor.

2. The improvement according to claim 1 wherein the test chamber is openable and closable independently of the said pressure means.

3. The improvement according to claim 1 wherein the rotor is smooth-surfaced.

4. The improvement according to claim 3 wherein means are provided for driving the rotor in rotation at different ascertained shear rates in relation to material in the test chamber.

5. Apparatus according to claim 1 wherein the said pressure means are also for exerting pressure to transfer material from the transfer chamber to the test chamber while the latter is closed.

6. Method of testing a material selected from the group consisting of unvulcanized natural rubber, unvulcanized synthetic rubber and elastomers having the same properties as unvulcanized rubber which includes placing a test sample within a test chamber of ascertained fixed volume and causing an interaction between a rotor in the chamber the sample and the walls of the chamber while exerting a controlled pressure on the sample from material in a transfer chamber via at least one communicating transfer port through a wall of the test chamber.

7. Method according to claim 6 wherein the test sample is placed into the already closed test chamber by transfer through said at least one transfer port, the said material exerting pressure from the transfer chamber being material for a next test sample.

8. Method according to claim 7 wherein the material to which pressure is subsequently applied in the transfer chamber is a test sample different from that which was transferred into the test chamber.

9. Method according to claim 8 wherein the test chamber is opened after completion of a test on material in the chamber and the tested material is removed therefrom while a subsequent test sample continues to be held in the transfer chamber.

10. Method according to claim 6 wherein the interaction between the material and the rotor includes driving the rotor at three different rates, a first rate being a higher rate, the second and third rates both being very substantially lower than the first rate and one being greater than the other by a factor sufficient to allow the calculation of the non-Newtonian index n of the material from the formula $$n = (\log S_{r2} - \log S_{r3})/\log f$$

wherein f is the factor between the second and third rates and $S_{r2}$ and $S_{r3}$ are shear stress at the second and third rates respectively.

11. Method according to claim 10 wherein the first rate is such as to induce shear up to 100 sec$^{-1}$ in the material.

12. Method according to claim 10 or claim 11 wherein after driving the rotor at the first rate the rotor is rotated in the reverse direction until there is substantially zero torque on the rotor, its reverse rotation being measured, whereby recovered shear strain can be recorded.

13. In apparatus for testing a material selected from the group consisting of unvulcanized natural rubber, unvulcanized synthetic rubber and elastomers having the same properties as unvulcanized rubber, said apparatus having a test chamber and a smooth-surfaced rotor in the test chamber, the improvement comprising wall means defining an ascertained fixed volume for the test chamber, at least one transfer port through a wall of the test chamber for rendering the transfer chamber in communication with the test chamber, means for exerting pressure on material in the transfer chamber, whereby a controlled pressure can be applied to and maintained on material in the test chamber through the at least one transfer port means for driving the rotor in rotation in one direction at different ascertained shear rates in relation to material in the test chamber, and means for recording back-rotation of the rotor in a direction opposite to that in which the drive means drive it.

* * * * *

UNITED STATES PATENT AND TRADEMARK OFFICE
CERTIFICATE OF CORRECTION

PATENT NO. : 4,275,600

DATED : June 30, 1981

INVENTOR(S) : Donald M. Turner, et al.

It is certified that error appears in the above-identified patent and that said Letters Patent are hereby corrected as shown below:

Column 5, line 21, delete "(1=F/CE)" and insert

--(1+F/CE)--

Signed and Sealed this

Fifteenth Day of September 1981

[SEAL]

Attest:

Attesting Officer

GERALD J. MOSSINGHOFF

Commissioner of Patents and Trademarks